US012642945B2

(12) United States Patent
Kojima et al.

(10) Patent No.: US 12,642,945 B2
(45) Date of Patent: Jun. 2, 2026

(54) BALLOON CATHETER

(71) Applicant: KANEKA CORPORATION, Osaka (JP)

(72) Inventors: Masahiro Kojima, Settsu (JP); Takahisa Hamabuchi, Osaka (JP)

(73) Assignee: KANEKA CORPORATION, Osaka (JP)

( * ) Notice: Subject to any disclaimer, the term of this patent is extended or adjusted under 35 U.S.C. 154(b) by 211 days.

(21) Appl. No.: 18/708,042

(22) PCT Filed: Oct. 31, 2022

(86) PCT No.: PCT/JP2022/040652
§ 371 (c)(1),
(2) Date: May 7, 2024

(87) PCT Pub. No.: WO2023/085150
PCT Pub. Date: May 19, 2023

(65) Prior Publication Data
US 2025/0256072 A1 Aug. 14, 2025

(30) Foreign Application Priority Data

Nov. 9, 2021 (JP) ................................. 2021-182761

(51) Int. Cl.
*A61M 25/10* (2013.01)
(52) U.S. Cl.
CPC ................................ *A61M 25/1002* (2013.01)
(58) Field of Classification Search
CPC .......... A61M 25/1002; A61M 25/1027; A61M 25/1029; A61M 25/104;

(Continued)

(56) References Cited

U.S. PATENT DOCUMENTS

2009/0234283 A1    9/2009    Burton et al.
2012/0215251 A1    8/2012    Burton et al.
(Continued)

FOREIGN PATENT DOCUMENTS

JP          2011-513031 A      4/2011
WO     WO 2020012850 A1      1/2020

OTHER PUBLICATIONS

First Office Action of CN20220017511 (Year: 2023).*
International Search Report (PCT/ISA/210) issued in PCT/2022/040652, dated Jan. 10, 2023.

*Primary Examiner* — Martin T Ton
(74) *Attorney, Agent, or Firm* — Birch, Stewart, Kolasch & Birch, LLP

(57) ABSTRACT

The balloon catheter includes: a shaft; and a balloon having a straight tube portion and a tapered portion, wherein the balloon has a wing-shaped portion and a protrusion on an outer surface, and a scattering intensity in each of the cross sections measured by laser Raman spectroscopy satisfies Expression (1): $I_{me} > I_{te}$ (1) where $I_{me}$ is Ia/Ib at a central part of a base end part of the protrusion on the straight tube portion, and $I_{tc}$ is Ia/Ib at a central part of a base end part of the protrusion on the tapered portion, Ia being a ratio of a peak intensity in the X direction to a peak intensity in the Y direction at a wavenumber of 1640 cm$^{-1}$, Ib being a ratio of a peak intensity in the X direction to a peak intensity in the Y direction at a wavenumber of 1440 cm$^{-1}$.

10 Claims, 4 Drawing Sheets

(58) Field of Classification Search
CPC .. A61M 2025/1004; A61M 2025/1086; A61M
2025/109; A61B 17/320725
See application file for complete search history.

(56) References Cited

U.S. PATENT DOCUMENTS

| | | | |
|---|---|---|---|
| 2013/0060127 A1* | 3/2013 | Burton ................. | A61M 25/10 |
| | | | 606/159 |
| 2017/0112526 A1 | 4/2017 | Burton et al. | |
| 2018/0296241 A1 | 10/2018 | Burton et al. | |
| 2021/0052850 A1* | 2/2021 | Ikoma ............... | A61M 25/0102 |
| 2021/0113820 A1 | 4/2021 | Okamoto et al. | |
| 2022/0184353 A1* | 6/2022 | Koga ................ | A61M 25/1002 |
| 2022/0218960 A1* | 7/2022 | Kojima ............. | A61M 25/1002 |
| 2025/0303125 A1* | 10/2025 | Motose .............. | A61M 25/104 |

* cited by examiner

[Fig. 1]
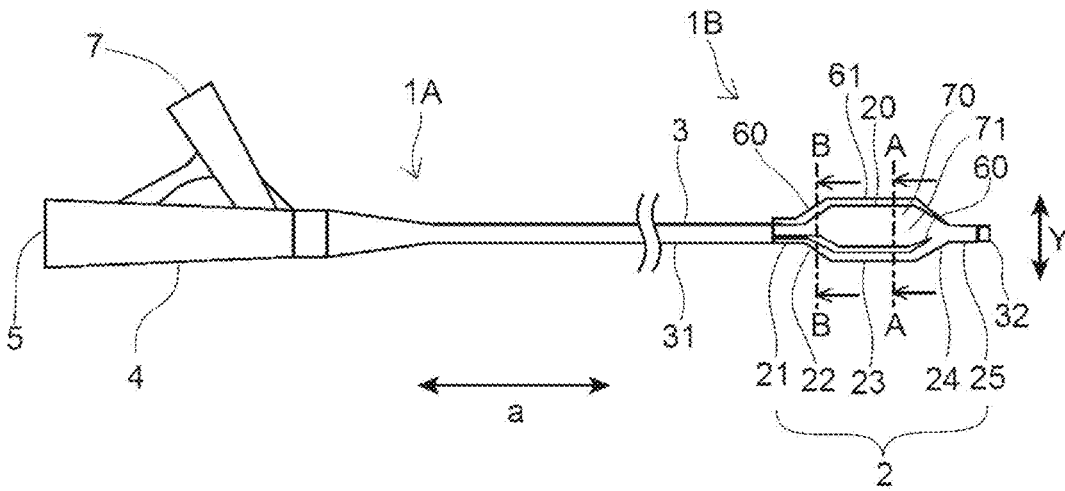
[Fig. 2]
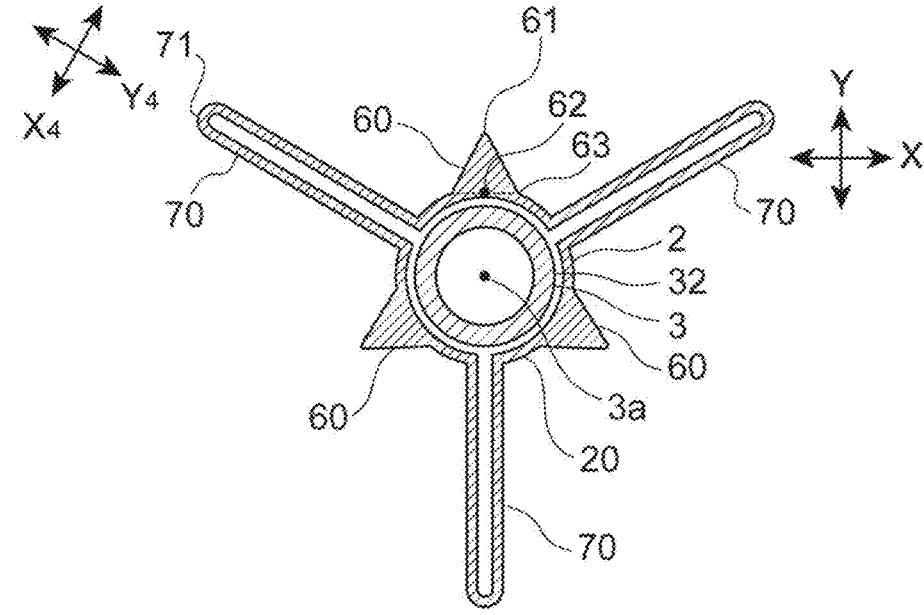

[Fig. 3]
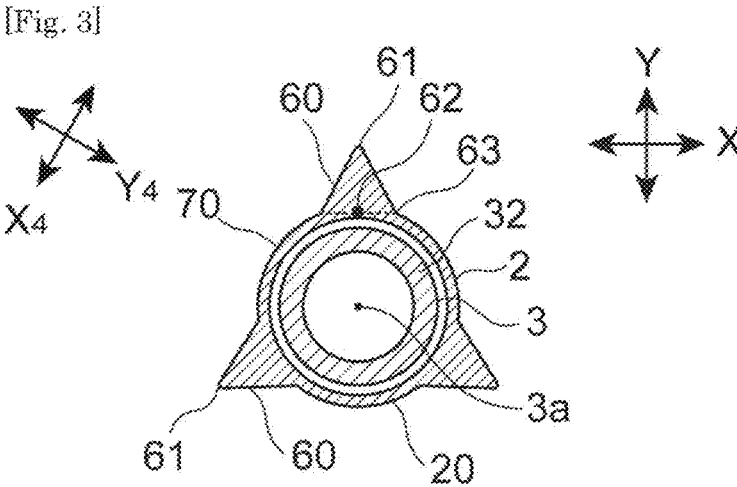
[Fig. 4]
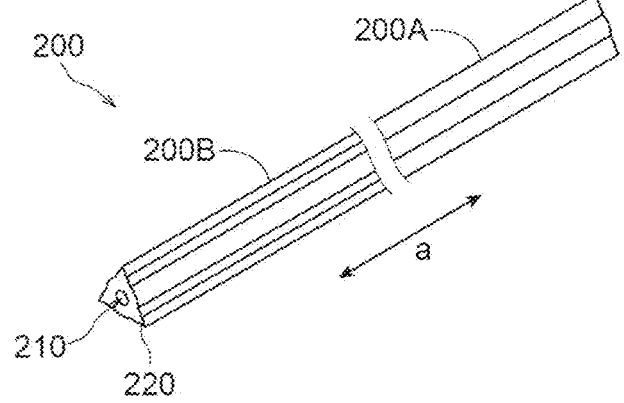
[Fig. 5]
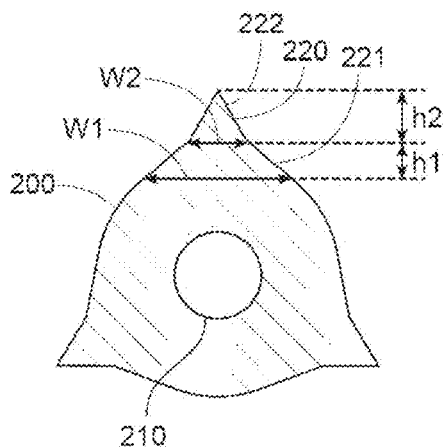

[Fig. 6]
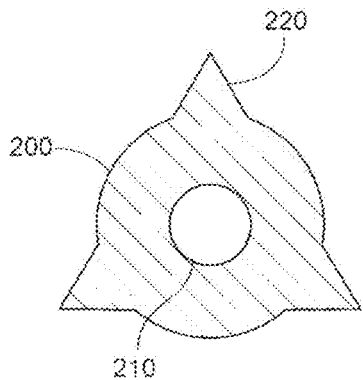
[Fig. 7]
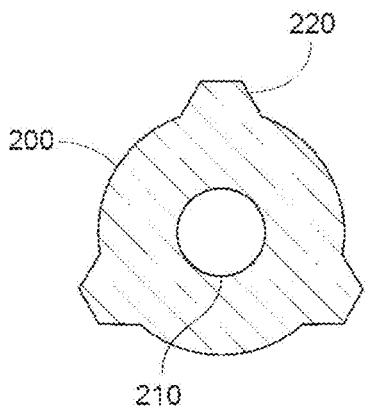
[Fig. 8]
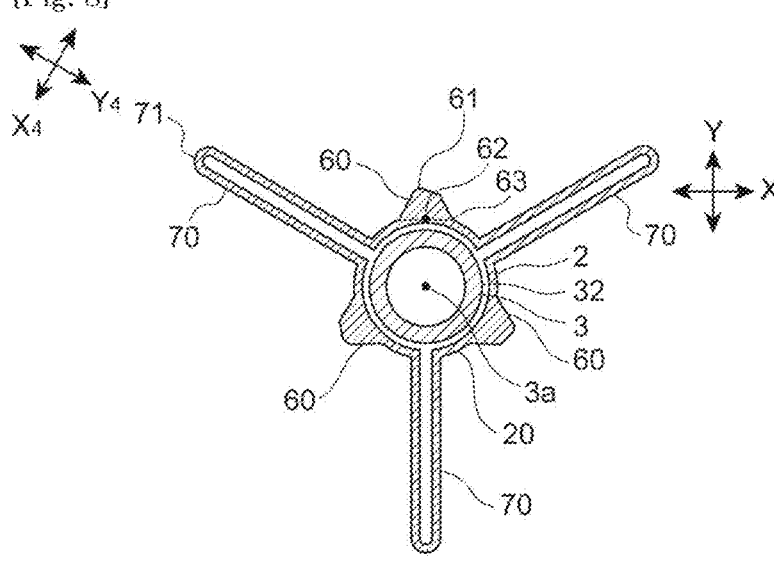

[Fig. 9]
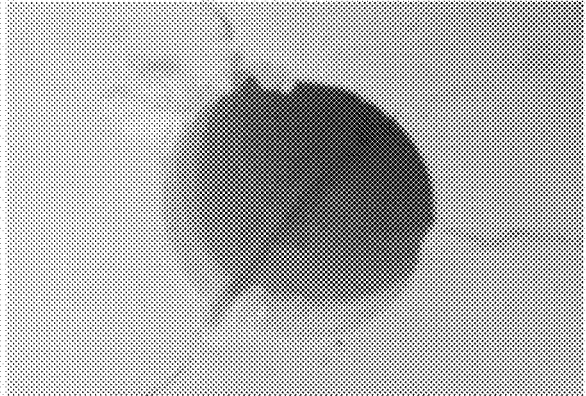
[Fig. 10]
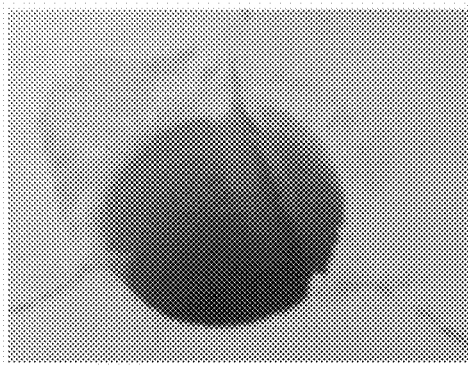
[Fig. 11]
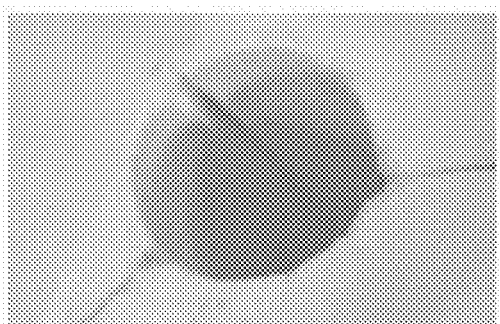
[Fig. 12]
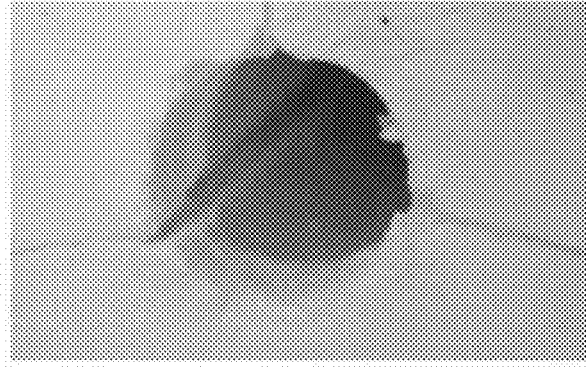

BALLOON CATHETER

TECHNICAL FIELD

The present invention relates to a balloon catheter.

BACKGROUND ART

Formation of a narrowed part that is hardened due to calcification or the like on the inner wall of the blood vessel may cause diseases such as angina pectoris and myocardial infarction. As one of methods for treating such diseases, angioplasty has been used for dilating the narrowed part using a balloon catheter. A balloon catheter used in the angioplasty includes a protrusion, a blade, and the like that penetrates and cuts a hardened narrowed part.

For example, Patent Document 1 discloses a balloon catheter including a protrusion provided to protrude on an outer surface of a balloon and linearly extending along the outer surface, in which the protrusion includes a first protrusion disposed on a straight tube portion and a second protrusion disposed on a tip-end tapered portion, and at least a part of the second protrusion in a longitudinal direction is a high protruding part having a larger protrusion amount from the outer surface than the first protrusion.

In addition, Patent Document 2 discloses a balloon catheter that includes a protuberance disposed along the outer surface of a balloon, fixed to the outer surface of the balloon at an interface region, and including a dilation element and a connector, the dilation element extending away from the outer surface of the balloon and defined by a second effective width, the connector connecting the dilation element to the outer surface of the balloon at the interface region, the connector being defined by a first effective width less than the second effective width of the dilation element.

RELATED ART DOCUMENT

Patent Documents

Patent Document 1: WO 2020/012850 A
Patent Document 2: JP-A-2011-513031

SUMMARY OF THE INVENTION

Problems to be Solved by the Invention

Conventional balloon catheters employ a protrusion having high rigidity due to a shape, a metal blade having higher hardness than a balloon body, a resin, or the like as a dilation element, and thus, the protrusion or the dilation element pushed back due to the hardness of a lesion may be buried into the balloon when the balloon is expanded by application of pressure. Therefore, it may be difficult to finely adjust the position of the balloon at a narrowed part, and it may be more difficult to sufficiently penetrate the protrusion or the dilation element into the narrowed part. The present invention has been made in view of the above problem, and an object of the present invention is to provide a balloon catheter that facilitates fine adjustment of a position of a balloon in a hardened narrowed part in a blood vessel and facilitates cutting of the narrowed part.

Solutions to the Problems

A balloon catheter according to an embodiment of the present invention capable of solving the above problem is as follows.

[1] A balloon catheter comprising:
a shaft having a distal portion and a proximal portion; and
a balloon located at the distal portion of the shaft and having a straight tube portion and at least one tapered portion,
wherein
the balloon has a wing-shaped portion having a wing shape in a contracted state and has a protrusion on an outer surface, and in a cross section in a direction perpendicular to an axial direction of the straight tube portion and a cross section in a direction perpendicular to an axial direction of the tapered portion, when a direction toward a center of the shaft from an apex of the protrusion is a Y direction and a direction perpendicular to the Y direction is an X direction, a scattering intensity in each of the cross sections measured by laser Raman spectroscopy satisfies Expression (1):

$$I_{mc} > I_{tc} \qquad (1)$$

where $I_{me}$ is a value of Ia/Ib at a central part in a circumferential direction of a base end part of the protrusion on the straight tube portion, and $I_{te}$ is a value of Ia/Ib at a central part in a circumferential direction of a base end part of the protrusion on the tapered portion,
Ia being a ratio of a peak intensity at a wavenumber of $1640 \pm 10$ cm$^{-1}$ in the X direction to a peak intensity at a wavenumber of $1640 \pm 10$ cm$^{-1}$ in the Y direction, Ib being a ratio of a peak intensity at a wavenumber of $1440 \pm 10$ cm$^{-1}$ in the X direction to a peak intensity at a wavenumber of $1440 \pm 10$ cm$^{-1}$ in the Y direction.

When the straight tube portion of the balloon satisfies Expression (1) as described above, the central part in the circumferential direction of the base end part of the protrusion on the straight tube portion has excellent rigidity because of a large orientation of higher order structures, and as a result, the protrusion is less likely to be buried in the balloon when the narrowed part is cut. On the other hand, when the tapered portion of the balloon satisfies Expression (1), the central part in the circumferential direction of the base end part of the protrusion on the tapered portion has relatively a small orientation and appropriate flexibility, and as a result, the protrusion on the tapered portion is less likely to be caught in the narrowed part, so that the position of the balloon can be easily finely adjusted. That is, due to the above configuration, a balloon catheter that facilitates fine adjustment of a position of a balloon in a hardened narrowed part in a blood vessel and facilitates cutting of the narrowed part can be provided. The balloon catheter according to the embodiment of the present invention is preferably configured as described in any one of items [2] to [10] below.

[2] The balloon catheter according to [1], wherein the scattering intensity in each of the cross sections measured by laser Raman spectroscopy satisfies Expression (2):

$$I_{me} > I_{te} \qquad (2)$$

where $I_{me}$ is a value of Ia/Ib at one end part in the circumferential direction of the base end part of the protrusion on the straight tube portion, and $I_{te}$ is a value of Ia/Ib at one end part in the circumferential direction of the base end part of the protrusion of the protrusion on the tapered portion, Ia and Ib being identical to the Ia and the Ib described in the preceding item.

[3] The balloon catheter according to [1] or [2], wherein the scattering intensity in each of the cross sections measured by laser Raman spectroscopy satisfies Expression (3):

$$I_{mp} > I_{tp} \tag{3}$$

where $I_{mp}$ is a value of Ia/Ib at the apex of the protrusion on the straight tube portion, and $I_{tp}$ is a value of Ia/Ib at the apex of the protrusion on the tapered portion, Ia and Ib being identical to the Ia and the Ib described in the preceding item.

[4] The balloon catheter according to any one of items [1] to [3], wherein when a direction toward the center of the shaft from an apex of the wing-shaped portion is an $Y_4$ direction and a direction perpendicular to the $Y_4$ direction is a $X_4$ direction in the cross sections, the scattering intensity in each of the cross sections measured by laser Raman spectroscopy satisfies Expression (4):

$$I_{tc} < I_{tq} \tag{4}$$

where $I_{tc}$ is identical to the $I_{tc}$ in the preceding item, and $I_{tq}$ is a value of Ic/Id at the apex of the wing-shaped portion on the tapered portion, Ic being a ratio of a peak intensity at a wavenumber of $1640 \pm 10$ cm$^{-1}$ in the $X_4$ direction to a peak intensity at a wavenumber of $1640 \pm 10$ cm$^{-1}$ in the $Y_4$ direction, Id being a ratio of a peak intensity at a wavenumber of $1440 \pm 10$ cm$^{-1}$ in the $X_4$ direction to a peak intensity at a wavenumber of $1440 \pm 10$ cm$^{-1}$ in the $Y_4$ direction.

[5] The balloon catheter according to any one of items [1] to [4], wherein when a direction toward the center of the shaft from an apex of the wing-shaped portion is an $Y_4$ direction and a direction perpendicular to the $Y_4$ direction is a $X_4$ direction in the cross sections, the scattering intensity in each of the cross sections measured by laser Raman spectroscopy satisfies Expression (5):

$$I_{mc} > I_{mq} \tag{5}$$

where $I_{mc}$ is identical to the $I_{mc}$ in the preceding item, and $I_{mq}$ is a value of Ic/Id at the apex of the wing-shaped portion on the straight tube portion, Ic being a ratio of a peak intensity at a wavenumber of $1640 \pm 10$ cm$^{-1}$ in the $X_4$ direction to a peak intensity at a wavenumber of $1640 \pm 10$ cm$^{-1}$ in the $Y_4$ direction, Id being a ratio of a peak intensity at a wavenumber of $1440 \pm 10$ cm$^{-1}$ in the $X_4$ direction to a peak intensity at a wavenumber of $1440 \pm 10$ cm$^{-1}$ in the $Y_4$ direction.

[6] The balloon catheter according to any one of items [1] to [5], wherein the at least one tapered portion includes a proximal tapered portion located proximal to the straight tube portion and decreasing in diameter with distance from the straight tube portion, and a distal tapered portion located distal to the straight tube portion and decreasing in diameter with distance from the straight tube portion.

[7] The balloon catheter according to [6], wherein the balloon includes a proximal fixing portion located proximal to the proximal tapered portion and fixed to the shaft, and a distal fixing portion located distal to the distal tapered portion and fixed to the shaft.

[8] The balloon catheter according to [6], wherein the protrusion is disposed on at least the proximal tapered portion, the straight tube portion, and the distal tapered portion.

[9] The balloon catheter according to [7], wherein the protrusion is disposed on the proximal fixing portion, the proximal tapered portion, the straight tube portion, the distal tapered portion, and the distal fixing portion.

[10] The balloon catheter according to any one of items [1] to [9], wherein the protrusion is disposed in a region other than the wing-shaped portion of the balloon.

Effects of the Invention

Due to the above configuration, the present invention can provide a balloon catheter that facilitates fine adjustment of a position of a balloon in a hardened narrowed part in a blood vessel and facilitates cutting of the narrowed part.

BRIEF DESCRIPTION OF THE DRAWINGS

FIG. 1 is a side view of a balloon catheter according to an embodiment.

FIG. 2 is a cross-sectional view of the balloon catheter in FIG. 1 along a line A-A in a contracted state.

FIG. 3 is a cross-sectional view of the balloon catheter in FIG. 1 along a line B-B in an expanded state.

FIG. 4 is a perspective view of a parison before expansion according to the embodiment.

FIG. 5 is a cross-sectional view in a radial direction of a distal portion of the parison in FIG. 4.

FIG. 6 is a cross-sectional view in a radial direction of a proximal portion of the parison in FIG. 4.

FIG. 7 is a cross-sectional view of a modification of the cross section in FIG. 6.

FIG. 8 is a cross-sectional view of the parison illustrated in FIG. 7 after expansion.

FIG. 9 is a photograph as a substitute for drawing illustrating a state of a gypsum model after a balloon according to Example 1 is expanded in the gypsum model and removed.

FIG. 10 is another photograph as a substitute for drawing illustrating a state of the gypsum model after the balloon according to Example 1 is expanded in the gypsum model and removed.

FIG. 11 is a photograph as a substitute for drawing illustrating a state of a gypsum model after a balloon according to Example 2 is expanded in the gypsum model and removed.

FIG. 12 is another photograph as a substitute for drawing illustrating a state of the gypsum model after the balloon according to Example 2 is expanded in the gypsum model and removed.

MODE FOR CARRYING OUT THE INVENTION

The present invention will be described below in more detail by way of the following embodiments. However, the present invention is not limited to the following embodiments. It is obvious that the present invention can be carried out by making modifications, as appropriate, in accordance with the gist described above or later, and such modifications are also included in the technical scope of the present invention. Note that, in each drawing, reference signs for components and the like may be omitted for convenience of description, and in such a case, the specification and other drawings are to be referred to. Further, the dimensions of the various components in the drawings are provided for the purpose of facilitating the understanding of the feature of the present invention, and the dimensions may differ from the actual dimensions in some cases.

A balloon catheter according to the embodiment of the present invention includes: a shaft having a distal portion and a proximal portion; and a balloon located at the distal portion of the shaft and having a straight tube portion and at least one tapered portion, wherein the balloon has a wing-shaped portion having a wing shape in a contracted state and has a protrusion on an outer surface, and in a cross section in a direction perpendicular to an axial direction of the straight tube portion and a cross section in a direction perpendicular to an axial direction of the tapered portion, when a direction toward a center of the shaft from an apex of the protrusion is a Y direction and a direction perpendicular to the Y direction is an X direction, a scattering intensity in each of the cross sections measured by laser Raman spectroscopy satisfies Expression (1):

$$I_{mc} > I_{tc} \tag{1}$$

where $I_{me}$ is a value of Ia/Ib at a central part in a circumferential direction of a base end part of the protrusion on the straight tube portion, and $I_{te}$ is a value of Ia/Ib at a central part in a circumferential direction of a base end part of the protrusion on the tapered portion, Ia being a ratio of a peak intensity at a wavenumber of $1640\pm10$ cm$^{-1}$ in the X direction to a peak intensity at a wavenumber of $1640\pm10$ cm$^{-1}$ in the Y direction, Ib being a ratio of a peak intensity at a wavenumber of $1440\pm10$ cm$^{-1}$ in the X direction to a peak intensity at a wavenumber of $1440\pm10$ cm$^{-1}$ in the Y direction.

When the straight tube portion of the balloon satisfies Expression (1) as described above, the central part in the circumferential direction of the base end part of the protrusion on the straight tube portion has excellent rigidity because of a large orientation of higher order structures, and as a result, the protrusion is less likely to be buried in the balloon when the narrowed part is cut. On the other hand, when the tapered portion of the balloon satisfies Expression (1), the central part in the circumferential direction of the base end part of the protrusion on the tapered portion has relatively a small orientation and appropriate flexibility, and as a result, the protrusion on the tapered portion is less likely to be caught in the narrowed part, so that the position of the balloon can be easily finely adjusted. That is, due to the above configuration, a balloon catheter that facilitates fine adjustment of the position of the balloon in a hardened narrowed part in a blood vessel and facilitates cutting of the narrowed part can be provided.

The balloon catheter according to the embodiment will be described below with reference to FIGS. 1 to 3. FIG. 1 is a side view of the balloon catheter according to the embodiment after the balloon is expanded. FIG. 2 is a cross-sectional view of the balloon catheter in FIG. 1 along a line A-A in a contracted state before the balloon is expanded. FIG. 3 is a cross-sectional view of the balloon catheter in FIG. 1 along a line B-B after the balloon is expanded.

As illustrated in FIG. 1, the balloon catheter 1 includes a shaft 3 having a distal portion 1B and a proximal portion 1A, and a balloon 2 located at the distal portion 1B of the shaft 3 and having a straight tube portion 23 and tapered portions 22 and 24. The balloon catheter 1 is preferably configured such that a fluid is supplied to the inside of the balloon 2 through the shaft 3. For example, contraction and expansion of the balloon 2 can be controlled using a balloon pressurizer. The fluid may be a pressurized fluid pressurized by a pump or the like.

The shaft 3 preferably has a fluid flow path therein. The shaft 3 preferably further has an insertion path for a linear body such as a guide wire. Specifically, the shaft 3 preferably has an outer tube 31 and an inner tube 32. At least a proximal portion of the inner tube 32 is located in the outer tube 31. With this configuration, the inner tube 32 can function as an insertion path for the linear body, and a space between the inner tube 32 and the outer tube 31 can function as a fluid flow path. In this case, the inner tube 32 preferably extends from the distal end of the outer tube 31. Further, the distal side of the balloon 2 is preferably fixed to the inner tube 32, and the proximal side of the balloon 2 is preferably fixed to the outer tube 31.

The straight tube portion 23 preferably has substantially the same diameter in an axial direction a. In addition, the straight tube portion 23 preferably has a maximum diameter in the balloon 2 at the time of expansion. The straight tube portion 23 has the maximum diameter, and thus, when the balloon 2 is expanded at a lesion such as a narrowed part, the straight tube portion 23 sufficiently comes into contact with the lesion and can easily dilate the lesion.

The balloon 2 preferably has a proximal tapered portion 22 located proximal to the straight tube portion 23 and a distal tapered portion 24 located distal to the straight tube portion 23. The proximal tapered portion 22 and the distal tapered portion 24 preferably decrease in diameter with distance from the straight tube portion 23. The proximal tapered portion 22 and the distal tapered portion 24 facilitate movement of the balloon 2 in the body cavity. Note that the balloon 2 may have either the proximal tapered portion 22 or the distal tapered portion 24.

It is preferable that the balloon 2 includes a proximal fixing portion 21 located proximal to the proximal tapered portion 22 and fixed to the shaft 3, and a distal fixing portion 25 located distal to the distal tapered portion 24 and fixed to the shaft 3. For example, when the shaft 3 has the outer tube 31 and the inner tube 32, it is preferable that at least a part of the proximal fixing portion 21 is fixed to the outer tube 31 and at least a part of the distal fixing portion 25 is fixed to the inner tube 32.

As illustrated in FIG. 2, the balloon 2 has a wing-shaped portion 70 having a wing shape in the contracted state, and has a protrusion 60 on the outer surface. The wing-shaped portion 70 preferably has portions overlapping each other in the inner surface of the balloon 2 in a state where the balloon 2 is contracted. Further, it is preferable that the wing-shaped portion 70 is formed so as to be folded with, for example, an apex 71 as a fold.

The protrusion 60 is provided on the outer surface of the balloon 2. By expanding the balloon 2 in a calcified lesion or the like, the protrusion 60 can crack, for example, a calcified and hardened lesion to dilate the narrowed part.

The protrusion 60 is preferably located in a region other than the wing-shaped portion 70 as illustrated in FIGS. 1 and 2. Due to the protrusion 60 being positioned in a region other than the wing-shaped portion 70, the wing-shaped portion 70 and the protrusion 60 are located at different positions in the circumferential direction of the balloon 2 in the contracted state, by which the outer diameter of the balloon 2 can be reduced when the wing-shaped portion 70 of the balloon 2 is folded.

The maximum length of the protrusion 60 in the radial direction is preferably 1.2 times or more, more preferably 1.5 times or more, and still more preferably 2 times or more the thickness of a balloon body 20. This configuration makes it easy to make a cut in the narrowed part with an appropriate depth. On the other hand, the maximum length of the protrusion 60 in the radial direction may be 100 times or less, 50 times or less, 30 times or less, or 10 times or less. In addition, the length of the protrusion 60 in the radial direction may differ or may be constant in the axial direction a.

The shape of the protrusion 60 in the cross section along the line A-A and the cross section along the line B-B is preferably triangular, trapezoidal, semicircular, or semi-elliptical. The cross-sectional shape is more preferably a one-step tapered shape having only one tapered portion that is tapered in a direction from a center 3a of the shaft 3 toward an apex 61 of the protrusion 60.

As illustrated in FIG. 1, the protrusion 60 is preferably disposed on the straight tube portion 23 and at least one of the proximal tapered portion 22 and the distal tapered portion 24, more preferably disposed on the proximal tapered portion 22, the distal tapered portion 24, and the straight tube portion 23, and still more preferably disposed on the proximal fixing portion 21, the proximal tapered portion 22, the straight tube portion 23, the distal tapered portion 24, and the distal fixing portion 25. The number of the protrusions 60 may be one, or more than one. When the plurality of protrusions 60 is provided in the circumferential direction, the plurality of protrusions 60 is preferably spaced in the circumferential direction, and more preferably equally spaced in the circumferential direction.

The protrusion 60 preferably extends in the axial direction a on the outer surface of the balloon body 20 as illustrated in FIG. 1. This makes it easy to incise the narrowed part straight. Although not illustrated, the protrusion 60 may be disposed at different positions in the circumferential direction along the axial direction a, that is, spirally disposed on, for example, the outer surface of the balloon body 20 in the circumferential direction. With this configuration, the narrowed part can be incised obliquely.

In the cross section illustrated in FIG. 2 in a direction perpendicular to the axial direction a of the straight tube portion 23 and the cross section illustrated in FIG. 3 in a direction perpendicular to the axial direction a of the tapered portion 22, 24, when a direction toward the center 3a of the shaft 3 from the apex 61 of the protrusion 60 is a Y direction and a direction perpendicular to the Y direction is an X direction, a scattering intensity in each of the cross sections measured by laser Raman spectroscopy satisfies Expression (1):

$$I_{mc} > I_{tc} \tag{1}$$

where $I_{mc}$ is a value of Ia/Ib at a central part 62 in a circumferential direction of a base end part of the protrusion 60 on the straight tube portion 23, and $I_{te}$ is a value of Ia/Ib at the central part 62 in the circumferential direction of the base end part of the protrusion 60 on the tapered portion 22, 24, Ia being a ratio of a peak intensity at a wavenumber of $1640\pm10$ cm$^{-1}$ in the X direction to a peak intensity at a wavenumber of $1640\pm10$ cm$^{-1}$ in the Y direction, Ib being a ratio of a peak intensity at a wavenumber of $1440\pm10$ cm$^{-1}$ in the X direction to a peak intensity at a wavenumber of $1440\pm10$ cm$^{-1}$ in the Y direction.

In the spectrum obtained by laser Raman spectroscopy, the peak at a wavenumber of $1640\pm10$ cm$^{-1}$ is a peak derived from a C=O structure, and the peak at a wavenumber of $1440\pm10$ cm$^{-1}$ is a peak derived from a C—H structure. As the value of Ia/Ib calculated on the basis of the laser Raman spectroscopy is larger, the orientation of higher order structures in the balloon 2 is larger. Therefore, due to $I_{me}$ being greater than $I_{te}$ as represented by Expression (1) above, the central part 62 in the circumferential direction of the base end part of the protrusion 60 on the straight tube portion 23 has excellent rigidity because of a large orientation of higher order structures, and as a result, the protrusion 60 is less likely to be buried in the balloon. In addition, the central part 62 in the circumferential direction of the base end part of the protrusion 60 on the tapered portion 22, 24 has relatively a small orientation and thus has appropriate flexibility, and as a result, the protrusion 60 on the tapered portion 22, 24 is less likely to be caught in the narrowed part having a complicated shape, so that the position of the balloon 2 can be easily finely adjusted. To this end, $I_{me}$ is preferably 1.1 times or more, more preferably 1.2 times or more, and still more preferably 1.3 times or more $I_{te}$. On the other hand, $I_{me}$ is preferably 5 times or less, more preferably 3 times or less, and still more preferably 2 times or less $I_{te}$. With this configuration, the balloon 2 can be easily manufactured. Further, it is more preferable that both the proximal tapered portion 22 and the distal tapered portion 24 satisfy Expression (1) above, but only one of the tapered portions may satisfy Expression (1) above. In FIG. 2, a broken line indicates an imaginary line segment indicating the base end edge of the protrusion 60, and the central part 62 of the protrusion 60 is preferably located in a region on the imaginary line segment and away from both ends of the imaginary line segment by more than ¼ of the length of the imaginary line segment, and more preferably located at the center point of the imaginary line segment.

It is preferable that the scattering intensity in each of the cross sections measured by laser Raman spectroscopy satisfies Expression (2):

$$I_{me} > I_{te} \tag{2}$$

where $I_{me}$ is a value of Ia/Ib at one end part 63 in the circumferential direction of the base end part of the protrusion 60 on the straight tube portion 23, and $I_{te}$ is a value of Ia/Ib at one end part 63 in the circumferential direction of the base end part of the protrusion 60 on the tapered portion 22, 24, Ia and Ib being identical to the Ia and the Ib described above.

Due to $I_{me}$ being greater than $I_{te}$, one end part 63 in the circumferential direction of the base end part of the protrusion 60 on the straight tube portion 23 has excellent rigidity because of a large orientation of higher order structures, and as a result, the protrusion 60 is further less likely to be buried in the balloon. In addition, one end part 63 in the circumferential direction of the base end part of the protrusion 60 on the tapered portion 22, 24 has relatively a small orientation and thus has appropriate flexibility, and as a result, the protrusion 60 on the tapered portion 22, 24 is less likely to be caught in the narrowed part having a complicated shape, so that the position of the balloon 2 can be more easily finely adjusted. To this end, $I_{me}$ is preferably 1.1 times or more, and more preferably 1.2 times or more $I_{te}$. On the other hand, $I_{me}$ is preferably 5 times or less, more preferably 3 times or less, and still more preferably 2 times or less $I_{te}$. With this configuration, the balloon 2 can be easily manufactured. It is more preferable that both end parts of the base end part of the protrusion 60 in the circumferential direction satisfy Expression (2) above. Further, it is more preferable that both the proximal tapered portion 22 and the distal tapered portion 24 satisfy Expression (2) above, but only one of the tapered portions may satisfy Expression (2) above. In FIG. 2, the broken line indicates an imaginary line segment indicating the base end edge of the protrusion 60, and one end part 63 of the protrusion 60 is preferably located in a region on the imaginary line segment and within ¼ of the length of the imaginary line segment from one end of the imaginary line segment, and more preferably located at one end of the imaginary line segment.

It is preferable that the scattering intensity in each of the cross sections measured by laser Raman spectroscopy satisfies Expression (3):

$$I_{mp} > I_{tp} \qquad (3)$$

where $I_{mp}$ is a value of Ia/Ib at the apex 61 of the protrusion 60 on the straight tube portion 23, and $I_{tp}$ is a value of Ia/Ib at the apex 61 of the protrusion 60 on the tapered portion 22, 24, Ia and Ib being identical to the Ia and the Ib described above.

Due to $I_{mp}$ being greater than $I_{tp}$, the orientation of higher order structures of the apex 61 of the protrusion 60 on the straight tube portion 23 increases, and thus, the apex 61 is excellent in rigidity. As a result, it is easy to cut the hardened narrowed part. On the other hand, due to $I_{tp}$ being lower than $I_{mp}$, the apex 61 of the protrusion 60 on the tapered portion 22, 24 is less likely to be caught by the narrowed part, so that the position of the balloon 2 can be easily finely adjusted. To this end, $I_{mp}$ is preferably 1.01 times or more, and more preferably 1.02 times or more $I_{tp}$. On the other hand, $I_{mp}$ is preferably 3 times or less, and more preferably 2 times or less $I_{tp}$. With this configuration, the balloon 2 can be easily manufactured. Further, it is more preferable that both the proximal tapered portion 22 and the distal tapered portion 24 satisfy Expression (3) above, but only one of the tapered portions may satisfy Expression (3) above.

When a direction toward the center 3a of the shaft 3 from an apex 71 of the wing-shaped portion 70 is an $Y_4$ direction and a direction perpendicular to the $Y_4$ direction is a $X_4$ direction in the cross sections, the scattering intensity in each of the cross sections measured by laser Raman spectroscopy preferably satisfies Expression (4):

$$I_{tc} < I_{tq} \qquad (4)$$

where $I_{tc}$ is identical to the $I_{tc}$ described above, and Ing is a value of Ic/Id at the apex 71 of the wing-shaped portion 70 on the tapered portion 22, 24, Ic being a ratio of a peak intensity at a wavenumber of 1640±10 cm$^{-1}$ in the $X_4$ direction to a peak intensity at a wavenumber of 1640±10 cm$^{-1}$ in the $Y_4$ direction, Id being a ratio of a peak intensity at a wavenumber of 1440±10 cm$^{-1}$ in the $X_4$ direction to a peak intensity at a wavenumber of 1440±10 cm$^{-1}$ in the $Y_4$ direction.

As the values of Ia/Ib and Ic/Id calculated on the basis of the laser Raman spectroscopy are larger, the orientation of higher order structures in the balloon 2 is larger. Therefore, due to $I_{te}$ being lower than $I_{tq}$, the central part 62 in the circumferential direction of the base end part of the protrusion 60 on the tapered portion 22, 24 has relatively a small orientation and thus has appropriate flexibility, and as a result, the protrusion 60 on the tapered portion 22, 24 is less likely to be caught in the narrowed part having a complicated shape, so that the position of the balloon 2 can be easily finely adjusted. $I_{te}$ is preferably 0.95 times or less, and more preferably 0.90 times or less $I_{tq}$. On the other hand, $I_{te}$ may be 0.1 times or more, or 0.5 times or more $I_{tq}$. Further, it is more preferable that both the proximal tapered portion 22 and the distal tapered portion 24 satisfy Expression (4) above, but only one of the tapered portions may satisfy Expression (4) above.

When a direction toward the center 3a of the shaft 3 from the apex 71 of the wing-shaped portion 70 is an $Y_4$ direction and a direction perpendicular to the $Y_4$ direction is a $X_4$ direction in the cross sections, the scattering intensity in each of the cross sections measured by laser Raman spectroscopy preferably satisfies Expression (5):

$$I_{mc} > I_{mq} \qquad (5)$$

where $I_{mc}$ is identical to the $I_{mc}$ described above, and $I_{mq}$ is a value of Ic/Id at the apex 71 of the wing-shaped portion 70 on the straight tube portion, Ic being a ratio of a peak intensity at a wavenumber of 1640±10 cm$^{-1}$ in the $X_4$ direction to a peak intensity at a wavenumber of 1640±10 cm$^{-1}$ in the $Y_4$ direction, Id being a ratio of a peak intensity at a wavenumber of 1440±10 cm$^{-1}$ in the $X_4$ direction to a peak intensity at a wavenumber of 1440±10 cm$^{-1}$ in the $Y_4$ direction.

Due to $I_{me}$ being greater than $I_{mq}$, the central part 62 in the circumferential direction of the base end part of the protrusion 60 on the straight tube portion 23 has excellent rigidity because of a large orientation of higher order structures, and as a result, the protrusion 60 is less likely to be buried in the balloon. To this end, $I_{me}$ is preferably 1.01 times or more, more preferably 1.02 times or more, and still more preferably 1.03 times or more $I_{mq}$. On the other hand, $I_{me}$ may be 3 times or less, or 2 times or less $I_{mq}$.

It is preferable that the scattering intensity in each of the cross sections measured by laser Raman spectroscopy satisfies Expression (6):

$$I_{mc}/I_{tc} > I_{me}/I_{te} \qquad (6)$$

where $I_{mc}$, $I_{tc}$, $I_{me}$, and $I_{te}$ are identical to the $I_{mc}$, $I_{te}$, $I_{me}$, and $I_{te}$ described above.

Due to $I_{mc}/I_{te}$ being greater than $I_{me}/I_{te}$, the rigidity of the central part 62 in the circumferential direction of the base end part of the protrusion 60 on the straight tube portion 23 can be further improved. To this end, $I_{mc}/I_{te}$ is preferably 1.01 times or more, and more preferably 1.02 times or more $I_{me}/I_{te}$. On the other hand, $I_{mc}/I_{te}$ is preferably 3 times or less, and more preferably 2 times or less $I_{me}/I_{te}$. With this configuration, the balloon 2 can be easily manufactured. Further, it is more preferable that both the proximal tapered portion 22 and the distal tapered portion 24 satisfy Expression (6) above, but only one of the tapered portions may satisfy Expression (6) above. It is more preferable that both end parts of the base end part of the protrusion 60 in the circumferential direction satisfy Expression (6) above.

Expressions (1) to (6) do not need to be satisfied over the entire region of the straight tube portion 23 and the tapered portions 22 and 24 in the axial direction a, and a portion having excellent rigidity or a portion having appropriate flexibility may be provided as appropriate. For example, it is preferable that Expressions (1) to (6) above are satisfied in a region including a midpoint of the straight tube portion 23 or the tapered portions 22 and 24 in the axial direction a, a point at a distance of ⅓ of the length of the straight tube portion 23 or the tapered portions 22 and 24 from one end thereof in the axial direction a, a point at a distance of ¼ of the length of the straight tube portion 23 or the tapered portions 22 and 24 from one end thereof in the axial direction a, and the like. As a result, it is possible to provide a portion having excellent rigidity or a portion having appropriate flexibility at a desired position such as the center, a portion closer to the front end, or a portion closer to the rear end of the straight tube portion 23 or the tapered portions 22 and 24. The length of the region satisfying Expressions (1) to (6) in the axial direction a is not particularly limited, but is preferably ⅟₁₈ or more, more preferably ⅟₁₅ or more, and still more preferably ⅟₁₂ or more of the length of the straight tube portion 23 or the tapered portions 22 and 24 in the axial direction a. The term "Expressions (1) to (6)" mean: Expression (1); or Expression (1) and Expression (2), (3), (4), (5), (6), or a combination thereof. In the above region, it is preferable that Expression (1), or Expression (1) and Expression (2), (3), (4), (5), or a combination thereof are satisfied, and it is more preferable that: Expression (1); Expressions (1) and (2); Expressions (1) and (3); or Expressions (1), (2), and (3) are satisfied.

The balloon 2 preferably contains resin, rubber, or a mixture thereof, and is more preferably constituted by resin, rubber, or a mixture thereof. As the resin, a resin containing a C—H unit and a C═O unit is preferable. Examples of such resin include: a polyamide resin such as polyamide or a polyamide elastomer such as a polyether block amide copolymer; a polyester resin such as polyethylene terephthalate or a polyester elastomer; and a polyurethane resin such as polyurethane or a polyurethane elastomer. Among these resins, elastomers are more preferable. The balloon 2 may contain other resins, and examples thereof include a polyphenylene sulfide resin, a fluorine resin, a silicone resin, and a polyolefin resin such as polyethylene, polypropylene, and or ethylene-propylene copolymer. Examples of the rubber include natural rubber such as latex rubber. These materials may be used alone, or two or more of them may be used in combination. Among them, a polyamide resin, a polyester resin, a polyurethane resin, or a mixture thereof is more preferable, a polyamide resin, a polyurethane resin, or a mixture thereof is still more preferable, a polyamide resin is still more preferable, and a polyether block amide copolymer is particularly preferable. With this configuration, a portion having a large orientation of higher order structures can be easily formed.

The protrusion 60 is preferably made of the same material as the balloon body 20. This makes it possible to inhibit the protrusion 60 from damaging the outer surface of the balloon body 20 while maintaining the flexibility of the balloon 2. The balloon body 20 and the protrusion 60 are preferably integrally molded. This can prevent the protrusion 60 from falling off the balloon body 20.

The balloon 2 can be manufactured using, for example, a parison 200 that is made of resin and that has a thick portion 220 extending in the axial direction a as illustrated in FIG. 4. For example, the balloon 2 can be manufactured by placing the parison 200 in the inner cavity of a mold and performing blow molding. Specifically, the balloon 2 can be formed, for example, by placing the parison 200 in the inner cavity of the mold, inserting the thick portion 220 of the parison 200 into a groove having a predetermined shape of the mold, introducing a fluid into an inner cavity 210 of the parison 200, and expanding the parison 200 while heating. The width and height of the protrusion 60 can be adjusted by the thickness of the thick portion 220 of the parison 200 or the depth and shape of the groove of the mold. Examples of the fluid include air, nitrogen, and water. At the time of blow molding, it is preferable to heat the parison 200 at a temperature equal to or higher than the glass transition temperature of the resin. Note that the parison 200 may be extended in the axial direction a before the expansion. The expansion step of expanding the parison 200 may be performed only once or a plurality of times. When the expansion step is performed a plurality of times, different molds may be used for each expansion.

As illustrated in FIG. 5, the thick portion 220 at a distal portion 200B of the parison 200 preferably has a first tapered portion 221 that is tapered in a direction from the inner cavity 210 toward the apex of the thick portion 220 and a second tapered portion 222 that is located on the apex side of the thick portion 220 with respect to the first tapered portion 221 and is tapered in a direction from the inner cavity 210 toward the apex of the thick portion 220. The parison 200 has the two-step tapered portion as described above, whereby tension is easily applied to the first tapered portion 221 during blow molding. Thus, it is possible to increase the orientation in the vicinity of the base end part of the protrusion 60 obtained by blow molding. Although FIG. 5 illustrates the parison having a two-step tapered portion at the distal portion 200B of the parison 200, the region having the two-step tapered portion is not limited to the distal portion 200B. It is possible to use the parison 200 having a two-step tapered portion in at least a part corresponding to a region where it is desired to provide a portion excellent in rigidity in the straight tube portion 23.

When blow molding is performed, it is preferable to eliminate the two-step tapered shape of the parison 200 to form the protrusion 60 having a one-step tapered shape. As a result, the orientation in the vicinity of the central part 62 of the base end part of the protrusion 60 can be further increased. As a method for eliminating the two-step tapered shape of the parison 200, blow molding may be performed after only the second tapered portion 222 is fitted into the groove without fitting the first tapered portion 221 of the parison 200 into the groove in the inner cavity of the mold. The groove preferably has a V shape.

A width W1 of the base end part of the first tapered portion 221 is preferably 1.5 times or more, and more preferably 2.0 times or more a width W2 of the base end part of the second tapered portion 222. This makes it easy to apply tension to the first tapered portion 221 during blow molding. On the other hand, the width W1 may be 10 times or less, or 5 times or less the width W2.

A height h1 of the first tapered portion 221 is preferably 0.9 times or less, and more preferably 0.8 times or less a height h2 of the second tapered portion 222. This makes it easy to apply tension to the first tapered portion 221 during blow molding. On the other hand, the height h1 may be 0.1 times or more, or 0.2 times or more the height h2.

On the other hand, the thick portion 220 at a proximal portion 200A of the parison 200 preferably has a one-step tapered shape as illustrated in FIGS. 6 and 7. As a result, excessive orientation in the vicinity of the base end part of the protrusion 60 obtained by blow molding can be suppressed to maintain flexibility. Therefore, at least a part of the proximal portion 200A of the parison 200 may form at least a part of the proximal tapered portion 22 of the balloon 2. Furthermore, in a case where it is desired to also suppress the orientation of at least a part of the distal tapered portion 24, a part of the distal portion 200B of the parison 200 may have a one-step tapered shape, and the part may form the distal tapered portion 24. Note that FIG. 8 is a cross-sectional view after the parison 200 in FIG. 7 is expanded, and the protrusion 60 may have an indefinite shape as illustrated in FIG. 8.

The shaft 3 preferably includes resin, rubber, or a mixture thereof. Examples of the resin and rubber include polyamide resin, polyester resin, polyurethane resin, polyolefin resin, fluorine resin, vinyl chloride resin, silicone resin, and natural rubber. These materials may be used alone, or two or more of them may be used in combination. The shaft 3 preferably includes, among the above-mentioned materials, a polyamide resin, a polyolefin resin, a fluorine resin, a mixture thereof, or a laminate obtained by laminating layers of these resins. As a result, it is possible to improve the insertability of the balloon catheter 1 in the body cavity while improving the slippage of the surface of the shaft 3. Examples of a method for fixing the balloon 2 to the shaft 3 include bonding with an adhesive, welding, and fixing by crimping a ring-shaped member. The shaft 3 may include a metal tube, a single wire or a plurality of wire materials, a stranded wire material, or the like.

The balloon catheter 1 may have a hub 4 on the proximal side of the shaft 3 as illustrated in FIG. 1. The hub 4 may include a fluid injection portion 7 communicating with the flow path for the fluid supplied to the inside of the balloon 2, a guide wire insertion portion 5 communicating with the insertion path for the guide wire, and the like. With this configuration, it is possible to easily perform an operation of supplying a fluid into the balloon 2 to expand the balloon 2 and an operation of delivering the balloon 2 to a treatment site along the guide wire. The balloon catheter 1 is preferably a so-called over-the-wire type in which the guide wire is passed all over the region from the distal side to the proximal side of the shaft 3 as illustrated in FIG. 1, but may be a so-called rapid exchange type in which the guide wire is passed from the distal side to a position in the middle between the distal side and the proximal side of the shaft 3.

This application claims benefit of priority based on Japanese Patent Application No. 2021-182761 filed on Nov. 9, 2021. The entire contents of the specification of Japanese Patent Application No. 2021-182761 filed on Nov. 9, 2021 are incorporated herein by way of reference.

EXAMPLES

The present invention will be described below in more detail by way of the following examples. However, the present invention is not limited to the following examples. It is obvious that the present invention can be carried out by making modifications, as appropriate, in accordance with the gist described above or later, and such modifications are also included in the technical scope of the present invention.

Example 1

A parison, which is a tube for producing a balloon having a tubular portion with an inner diameter of 0.50 mm, an outer diameter of 1.00 mm, and an axial length of 300 mm and a thick portion, was produced by extrusion molding using a polyamide elastomer (PEBAX (registered trademark) 7233) manufactured by ARKEMA K.K. The thick portion of the parison has a first one-step tapered portion, a two-step tapered portion, and a second one-step tapered portion in this order from the proximal end toward the distal end, and the dimensions thereof are as follows.

First One-Step Tapered Portion (Portion for Forming the Proximal Fixing Portion 21 and the Proximal Tapered Portion 22)

Width of base end part of tapered portion: 0.3 mm

Height of tapered portion: 0.5 mm

Length in axial direction a: 5 mm

Two-Step Tapered Portion (Portion for Forming the Straight Tube Portion 23)

Width (W1) of base end part of first tapered portion: 1.0 mm

Width (W2) of base end part of second tapered portion: 0.5 mm

Height (h1) of first tapered portion: 0.2 mm

Height (h2) of second tapered portion: 0.3 mm

Length in axial direction a: 10 mm

Second Two-Step Tapered Portion (Portion for Forming the Distal Tapered Portion 24 and the Distal Fixing Portion 25)

Width of base end part of tapered portion: 0.5 mm

Height of tapered portion: 0.5 mm

Length in axial direction a: 5 mm

Next, the parison 200 was placed in the inner cavity of a mold. The mold includes an inner cavity and a V-shaped groove having the following dimensions in a portion corresponding to each portion of the balloon 2.

Inner Cavity in a Portion where the Proximal Fixing Portion 21 is to be Formed

Diameter: 1.0 mm

Length in axial direction: 5 mm

Inner Cavity in a Portion where the Proximal Tapered Portion 22 is to be Formed

Diameter of proximal end: 1.0 mm

Diameter of distal end: 2.75 mm Length in axial direction: 5 mm

Inner Cavity in a Portion where the Straight Tube Portion 23 is to be Formed

Diameter: 2.75 mm

Length in axial direction: 15 mm

Inner Cavity in a Portion where the Distal Tapered Portion 24 is to be Formed

Diameter of proximal end: 2.75 mm

Diameter of distal end: 1.0 mm

Length in axial direction: 5 mm

Inner Cavity in a Portion where the Distal Fixing Portion 25 is to be Formed

Diameter: 1.0 mm

Length in axial direction: 5 mm

V-Shaped Groove for a Portion where the Protrusion 60 is to be Formed

Depth: 0.8 mm
   Maximum width: 0.5 mm
   Length in axial direction: 35 mm

Using the mold, biaxial stretch blow molding was performed on the parison 200 at 100° C. to produce the balloon 2. Next, the proximal tapered portion 22 and the straight tube portion 23 of the balloon 2 were cut, and the obtained samples were embedded in a resin. Thereafter, observation cross sections were produced using a freezing ultramicrotome (UC6) manufactured by Leica Corporation. Using a Raman spectrometer, the peak intensity of a peak present within a wavenumber range of 1630 to 1650 $cm^{-1}$ and the peak intensity of a peak present within a wavenumber range of 1430 to 1450 $cm^{-1}$ in the X direction and the Y direction in each of the apex 61 of the protrusion 60, the central part 62 in the circumferential direction of the base end part, and one end part 63 in the circumferential direction of the base end part were obtained. Details of the measurement are as follows.

Apparatus: Raman spectrometer (in Via™ Qontor manufactured by Renishaw K.K.)
   Microscope: DM2700 manufactured by Leica Microsystems Objective lens: ×100
   Beam diameter: 1 μm
   Laser power: 100%
   Exposure time: 30 s
   Number of scans: 1
   Light source: Semiconductor laser 532 nm The values of $I_{mp}$, $I_{me}$, $I_{me}$, $I_{mq}$, $I_{tp}$, $I_{te}$, $I_{te}$, and $I_{tq}$ according to the above (1) to (6) were calculated based on the peak intensities obtained by the above measurement. The results are shown in Table 1.

As shown in Table 1, the balloon 2 satisfied Expression (1). When the balloon 2 was fixed to a shaft and the balloon 2 was expanded in a gypsum model, the protrusion 60 penetrated into the gypsum model. Furthermore, after the balloon was contracted and removed from the inside of the model, a shape generated by penetration of the protrusion 60 was confirmed as illustrated in FIGS. 9 and 10. As described above, the protrusion 60 of the straight tube portion 23 was hardly buried in the balloon 2. On the other hand, the central parts 62 of the base end parts of the protrusions 60 on the proximal tapered portion 22 and the distal tapered portion 24 were relatively flexible. Therefore, when the balloon 2 was moved in the gypsum model simulating a narrowed part before the expansion, the balloon 2 could be smoothly inserted and removed without being caught.

Example 2

A balloon was prepared in the same manner as in Example 1 except that extrusion molding was performed using a polyamide elastomer (Rilsamid (registered trademark) PA12) manufactured by ARKEMA K.K., and the width (W1) of the base end part of the first tapered portion of the parison 200 was set to 0.7 mm. The peak intensity of each portion was obtained, and the values of $I_{mp}$, $I_{mc}$, $I_{me}$, $I_{tp}$, $I_{tc}$, and $I_{te}$ according to (1) to (6) above according to (1) to (6) above were calculated. The results are shown in Table 2.

TABLE 1

| | | | | | Ratio of Peak intensity | | | |
| --- | --- | --- | --- | --- | --- | --- | --- | --- |
| | | Direction of | Peak intensity | | (Ia:X/Y) (Ic:X4/Y4) | (Ib:X/Y) (Id:X4/Y4) | Orientation parameter Ia/Ib | |
| Position of measurement | | measurement | 1640 $cm^{-1}$ | 1440 $cm^{-1}$ | 1640 $cm^{-1}$ | 1440 $cm^{-1}$ | | Ic/Id |
| Straight tube portion | Apex of protrusion | X | 1408.98 | 2887.8 | 1.30 | 0.98 | $I_{mp}$ | 1.33 |
| | | Y | 1082.56 | 2943.04 | | | | |
| | Central part in circumferential direction of base end part of protrusion | X | 2405.26 | 2418.08 | 4.49 | 0.78 | $I_{mc}$ | 5.74 |
| | | Y | 535.546 | 3088.09 | | | | |
| | One end part in circumferential direction of base end part of protrusion | X | 1904.97 | 2691.28 | 2.96 | 0.76 | $I_{me}$ | 3.91 |
| | | Y | 643.888 | 3557.79 | | | | |
| | Apex of wing-shaped portion | $X_4$ | 1169.91 | 1349 | 2.95 | 0.53 | $I_{mq}$ | 5.54 |
| | | $Y_4$ | 395.957 | 2528.9 | | | | |
| Tapered portion | Apex of protrusion | X | 1150.49 | 2094.81 | 0.79 | 0.63 | $I_{tp}$ | 1.26 |
| | | Y | 1452.85 | 3322.86 | | | | |
| | Central part in circumferential direction of base end part of protrusion | X | 2319.35 | 2384.94 | 3.17 | 0.74 | $I_{tc}$ | 4.30 |
| | | Y | 730.531 | 3230.33 | | | | |
| | One end part in circumferential direction of base end part of protrusion | X | 1524.87 | 3234.03 | 2.58 | 0.85 | $I_{te}$ | 3.04 |
| | | Y | 591.831 | 3821.95 | | | | |
| | Apex of wing-shaped portion | $X_4$ | 1557.76 | 2473.79 | 4.67 | 0.91 | $I_{tq}$ | 5.15 |
| | | $Y_4$ | 333.605 | 2728.48 | | | | |

TABLE 2

| | | | | Ratio of Peak intensity | | |
| Position of measurement | Direction of measurement | Peak intensity 1640 cm⁻¹ | 1440 cm⁻¹ | (Ia:X/Y)(Ic:X4/Y4) 1640 cm⁻¹ | (Ib:X/Y)(Id:X4/Y4) 1440 cm⁻¹ | Orientation parameter Ia/Ib |
|---|---|---|---|---|---|---|
| Straight tube portion Apex of protrusion | X | 8261.8 | 18218.4 | 1.05 | 0.92 | $I_{mp}$  1.14 |
| | Y | 7892.69 | 19823.1 | | | |
| Central part in circumferential direction of base end part of protrusion | X | 6665.45 | 17291.2 | 1.81 | 0.76 | $I_{mc}$  2.38 |
| | Y | 3677.14 | 22707.4 | | | |
| One end part in circumferential direction of base end part of protrusion | X | 7566.51 | 19344.5 | 2.44 | 0.87 | $I_{me}$  2.81 |
| | Y | 3098.6 | 22287.8 | | | |
| Tapered portion Apex of protrusion | X | 6672.52 | 12692.9 | 0.71 | 0.86 | $I_{tp}$  0.83 |
| | Y | 9428.86 | 14816.2 | | | |
| Central part in circumferential direction of base end part of protrusion | X | 15220.8 | 29521 | 1.35 | 0.96 | $I_{tc}$  1.40 |
| | Y | 11296.5 | 30627.9 | | | |
| One end part in circumferential direction of base end part of protrusion | X | 16650.5 | 26068 | 1.73 | 0.91 | $I_{te}$  1.91 |
| | Y | 9598.16 | 28637.3 | | | |

As shown in Table 2, the balloon according to Example 2 satisfied Expression (1). When this balloon was fixed to a shaft and the balloon was expanded in a gypsum model, the protrusion penetrated into the gypsum model. Furthermore, after the balloon was contracted and removed from the inside of the model, a shape generated by penetration of the protrusion was confirmed as illustrated in FIGS. 11 and 12. As described above, the protrusion of the straight tube portion was hardly buried in the balloon. On the other hand, the central parts of the base end parts of the protrusions on the proximal tapered portion and the distal tapered portion were relatively flexible. Therefore, when the balloon was moved in the gypsum model simulating a narrowed part before the expansion, the balloon could be smoothly inserted and removed without being caught.

DESCRIPTION OF REFERENCE SIGNS

1: Balloon catheter
1A: Proximal portion
1B: Distal portion
2: Balloon
3: Shaft
3*a*: Center of shaft
4: Hub
5: Guide wire insertion portion
7: Fluid injection portion
20: Balloon body
21: Proximal fixing portion
22: Proximal tapered portion
23: Straight tube portion
a: Axial direction
24: Distal tapered portion
25: Distal fixing portion
31: Outer tube
32: Inner tube
60: Protrusion
61: Apex of protrusion
62: Central part in circumferential direction of base end part of protrusion

63: One end part in circumferential direction of base end part of protrusion
70: Wing-shaped portion
71: Apex of wing-shaped portion
200: Parison
200A: Proximal portion of parison
200B: Distal portion of parison
210: Inner cavity of parison
220: Thick portion of parison
221: First tapered portion
222: Second tapered portion
W1: Width of base end part of first tapered portion
W2: Width of base end part of second tapered portion
h1: Height of first tapered portion
h2: Height of second tapered portion

The invention claimed is:

1. A balloon catheter comprising:
a shaft having a distal portion and a proximal portion; and
a balloon located at the distal portion of the shaft and having a straight tube portion and at least one tapered portion, wherein
the balloon has a wing-shaped portion, which has a wing shape, in a contracted state and has a protrusion on an outer surface, and in a cross section in a direction perpendicular to an axial direction of the straight tube portion and a cross section in a direction perpendicular to an axial direction of the tapered portion, a scattering intensity in each of the cross sections measured by laser Raman spectroscopy satisfies Expression (1):

$$I_{mc} > I_{tc} \qquad (1)$$

where $I_{mc}$ is a value of Ia/Ib at a central part in a circumferential direction of a base end part of the protrusion on the straight tube portion, and $I_{tc}$ is a value of Ia/Ib at a central part in a circumferential direction of a base end part of the protrusion on the tapered portion, Ia being a ratio of a peak intensity at a wavenumber of 1640±10 cm$^{-1}$ in a X direction to a peak intensity at a wavenumber of 1640±10 cm$^{-1}$ in a Y direction, Ib being a ratio of a peak intensity at a wavenumber of 1440±10 cm$^{-1}$ in the X direction to a peak intensity at a wavenumber of 1440±10 cm$^{-1}$ in the Y direction, where a direction toward a center of the shaft from an apex of the protrusion is the Y direction and a direction perpendicular to the Y direction is the X direction.

2. The balloon catheter according to claim 1, wherein the scattering intensity in each of the cross sections measured by laser Raman spectroscopy satisfies Expression (2):

$$I_{me} > I_{te} \tag{2}$$

where $I_{me}$ is a value of Ia/Ib at one end part in the circumferential direction of the base end part of the protrusion on the straight tube portion, and $I_{te}$ is a value of Ia/Ib at one end part in the circumferential direction of the base end part of the protrusion of the protrusion on the tapered portion, Ia and Ib being identical to the Ia and the Ib described in claim 1.

3. The balloon catheter according to claim 1, wherein the scattering intensity in each of the cross sections measured by laser Raman spectroscopy satisfies Expression (3):

$$I_{mp} > I_{tp} \tag{3}$$

where $I_{mp}$ is a value of Ia/Ib at the apex of the protrusion on the straight tube portion, and $I_{tp}$ is a value of Ia/Ib at the apex of the protrusion on the tapered portion, Ia and Ib being identical to the Ia and the Ib described in claim 1.

4. The balloon catheter according to claim 1, wherein scattering intensity in each of the cross sections measured by laser Raman spectroscopy satisfies Expression (4)

$$I_{tc} < I_{tq} \tag{4}$$

where $I_{tc}$ is identical to the $I_{tc}$ in claim 1, and $I_{tq}$ is a value of Ic/Id at the apex of the wing-shaped portion on the tapered portion, Ic being a ratio of a peak intensity at a wavenumber of 1640±10 cm$^{-1}$ in a X$_4$ direction to a peak intensity at a wavenumber of 1640±10 cm$^{-1}$ in a Y$_4$ direction, Id being a ratio of a peak intensity at a wavenumber of 1440±10 cm$^{-1}$ in the X$_4$ direction to a peak intensity at a wavenumber of 1440±10 cm$^{-1}$ in the Y$_4$ direction, where a direction toward the center of the shaft from an apex of the wing-shaped portion is the Y$_4$ direction, and a direction perpendicular to the Y$_4$ direction is the X$_4$ direction in the cross sections.

5. The balloon catheter according to claim 1, wherein, the scattering intensity in each of the cross sections measured by laser Raman spectroscopy satisfies Expression (5):

$$I_{mc} > I_{mq} \tag{5}$$

where $I_{mc}$ is identical to the $I_{mc}$ in claim 1, and $I_{mq}$ is a value of Ic/Id at the apex of the wing-shaped portion on the straight tube portion, Ic being a ratio of a peak intensity at a wavenumber of 1640±10 cm$^{-1}$ in a X$_4$ direction to a peak intensity at a wavenumber of 1640±10 cm$^{-1}$ in a Y$_4$ direction, Id being a ratio of a peak intensity at a wavenumber of 1440±10 cm$^{-1}$ in the X$_4$ direction to a peak intensity at a wavenumber of 1440±10 cm$^{-1}$ in the Y$_4$ direction, where a direction toward the center of the shaft from an apex of the wing-shaped portion is the Y$_4$ direction, and a direction perpendicular to the Y$_4$ direction is the X$_4$ direction in the cross sections.

6. The balloon catheter according to claim 1, wherein the at least one tapered portion includes a proximal tapered portion located proximal to the straight tube portion and decreasing in diameter with distance from the straight tube portion, and a distal tapered portion located distal to the straight tube portion and decreasing in diameter with distance from the straight tube portion.

7. The balloon catheter according to claim 6, wherein the balloon includes a proximal fixing portion located proximal to the proximal tapered portion and fixed to the shaft, and a distal fixing portion located distal to the distal tapered portion and fixed to the shaft.

8. The balloon catheter according to claim 6, wherein the protrusion is disposed on at least the proximal tapered portion, the straight tube portion, and the distal tapered portion.

9. The balloon catheter according to claim 7, wherein the protrusion is disposed on the proximal fixing portion, the proximal tapered portion, the straight tube portion, the distal tapered portion, and the distal fixing portion.

10. The balloon catheter according to claim 1, wherein the protrusion is disposed in a region other than the wing-shaped portion of the balloon on the outer surface of the balloon.

\* \* \* \* \*